United States Patent [19]
Miki et al.

[11] Patent Number: 5,824,863
[45] Date of Patent: Oct. 20, 1998

[54] SEED COAT-SPECIFIC CRYPTIC PROMOTER IN TOBACCO

[75] Inventors: Brian Miki, Ottawa; V. N. Iyer, Saskatoon; Pierre Fobert, Ottawa, all of Canada

[73] Assignees: Her Majesty the Queen in right of Canada, as represented by Agriculture; Agri-Food Canada, both of Ottawa, Canada

[21] Appl. No.: 441,597

[22] Filed: May 15, 1995

[51] Int. Cl.$^6$ .............................. A01H 5/00; C12N 15/82
[52] U.S. Cl. .................. 800/205; 536/24.1; 435/69.1; 435/172.3; 435/320.1; 435/418; 435/419
[58] Field of Search .......................... 800/205; 536/24.1; 435/69.1, 172.3, 240.4, 320.1, 418, 419

[56] References Cited

PUBLICATIONS

T–DNA tagging of a seed coat–specific cryptic promoter in tobacco. The Plant Journal, (1994) 6(4), 567–577.
Detection of gene regulatory signals in plant revealed by T–DNA–mediated fusions. Plant Molecular Biology, (1991) 17:837–851.
Programs and Abstracts, Third International Congress of Plant Molecular Biology. Molecular Biology of Plant Growth and Development. 6–11 Oct. 1991, Tucson, Arizona, U.S.A.
T–DNA tagging of promoter–like regions. Poster Abstract Form. P. Fobert et al.
Kim et al. (1994) Plant Mol Biol 24: 105–117.

*Primary Examiner*—Elizabeth F. McElwain
*Attorney, Agent, or Firm*—Heslin & Rothenberg, P.C.

[57] ABSTRACT

T-DNA tagging with a promoterless β-glucuronidase (GUS) gene generated a transgenic Nicotiana tabacum plant that expressed GUS activity only in developing seed coats. Cloning and deletion analysis of the GUS fusion revealed that the promoter responsible for seed coat specificity was located in the plant DNA proximal to the GUS gene. Analysis of the region demonstrated that the seed coat-specificity of GUS expression in this transgenic plant resulted from T-DNA insertion next to a cryptic promoter. This promotor is useful in controlling the expression of genes to the developing seed coat in plant seeds.

9 Claims, 9 Drawing Sheets

```
                                                             1   2
         XbaI                                              ┌─────┬─────→
  1   TCTAGACTTGTCTTTTCTTTACATAATCCTCTTCTTCTTTTTTTGTTAGTTTCTTCTGT

61   TTTATCCAAAAAACGAATTATTGATTAAGAAATACACCAGACAAGTTTTTTACTTCTTTT
         1   2
      ┌───┬─────→
121   TCTTTTTTTTTTTGTGGTAAAAAATTACACCTGGACAAGTTTATCACGAAAATGAAAATT
                                                         8
                                                       ┌─────→
181   GCTATTTAAGGGATGTAGTTCCGGACTATTTGGAAGATAAGTGTTAACAAAATAAATAAA
                            6
                          ┌───┬3────→                       7
                                                          ┌───┬4
241   TAAAAAGTTTATACAGTTAGATCTCTCTATAACAGTCATCCTTATTTATAACAATACTTT
      7
      ┌───→                           4
      4                             ┌───┬3─────→
301   ACTATAACCGTCAAATTTATTTTGAAACAAAATTTTCATGTTATGTTACTATAACAGTAT

6
                                          ←─┴───┐
361   TTTATTATAGCAACCAAAAAATATCGAAACAGATACGATTGTTATAGAGCGATTTGATTG

SnaB1
421   TATCATTATCCACATATTTTCGTAAGCCCAATTACTCCTCCTACGTACGATGAAAGTAAA

481   CCAATTTAAAGTTGCAAAAATCCAATAGATTTCAATACTTCTTCAACTGGCGTTATGTTA

541   GGTAATGACTCCTTTTTAACTTTTCATCTTTAATTTGAAGTTTCTTTCATTAAAAGAAAG
      ┌5─XbaI──→                                    ┌5─XbaI──→
601   TTTCTAGAAGAGAAGTGTTTTAACACTTCTAGCTCTACTATTATCTGTGTTTCTAGAAGA
                                                              8
                                                           ←─┬──
661   AAAATAGAAAATGTGTCCACCTCAAAAACAACTAAAGGTGG GCAAATCTC CACCTATTTA
                           ↓    7
         ←─┐             ←─────┤
721   TTTTATTTTGGATTAATTAAGATATAGTAAAGATCAG TTATAAACG GAGTTTTGAGTTGA

781   TACAG TGAATTTTAAG ATGTGTACCGATTTAACTTTATTTACATTTATGTTTCGCACATA
      TATA                       ↓
841   TAAGAAGTCCGATTTGGAAATACTAGATTTTGTCAATCAGGCAATTCATGTGGTTGAAGA

901   ATTTAAGTTATATACAATGATGATATAAAGAATTTTTATACTATTAGTGCAAATTAATCG

957   ATTACTAAAAATTATTATTCTATTAATTTATGCTATC│GTGCCTCCCCAACCCGTCGACC
                                          │ATATCAAATTTAGTATTCCTTT
                                  *
1005  GCGGTACCCGGTGGTCAGTCCCTT ATG TTA CGT CCT GTA GAA ACC CCA ACC
                                M   L   R   P   V   E   T   P   T
```

SEED COAT-SPECIFIC CRYPTIC PROMOTER IN TOBACCO

FIELD OF THE INVENTION

This invention relates to a cryptic promoter identified from *Nicotiana tabacum* (tobacco). Specifically this invention relates to a seed coat-specific cryptic promoter isolated from tobacco.

BACKGROUND AND PRIOR ART

Bacteria from the genus Agrobacterium have the ability to transfer specific segments of DNA (T-DNA) to plant cells, where they stably integrate into the nuclear chromosomes. Analyses of plants harbouring the T-DNA have revealed that this genetic element may be integrated at numerous locations, and can occasionally be found within genes. One strategy which may be exploited to identify integration events within genes is to transform plant cells with specially designed T-DNA vectors which contain a reporter gene, devoid of cis-acting transcriptional and translational expression signals (i.e. promoterless), located at the end of the T-DNA. Upon integration, the initiation codon of the promoterless gene (reporter gene) will be juxtaposed to plant sequences. The consequence of T-DNA insertion adjacent to, and downstream of, gene promoter elements may be the activation of reporter gene expression. The resulting hybrid genes, referred to as T-DNA-mediated gene fusions, consist of unknown and thus un-characterized plant promoters residing at their natural location within the chromosome, and the coding sequence of a marker gene located on the inserted T-DNA (Fobert et al., 1991, Plant Mol. Biol. 17, 837–851).

It has generally been assumed that activation of promoterless or enhancerless marker genes result from T-DNA insertions within or immediately adjacent to genes. The recent isolation of several T-DNA insertional mutants (Koncz et al., 1992, *Plant Mol. Biol.* 20, 963–976; reviewed in Feldmann, 1991, *Plant J.* 1, 71–82; Van Lijsebettens et al., 1991, *Plant Sci.* 80, 27–37; Walden et al., 1991, *Plant J.* 1: 281–288; Yanofsky et al., 1990, *Nature* 346, 35–39), shows that this is the case for at least some insertions. However, other possibilities exist. One of these is that integration of the T-DNA activates silent regulatory sequences that are not associated with genes. Lindsey et al. (1993, *Transgenic Res.* 2, 33–47) referred to such sequences as "pseudo-promoters" and suggested that they may be responsible for activating marker genes in some transgenic lines.

Inactive regulatory sequences that are buried in the genome but with the capability of being functional when positioned adjacent to genes have been described in a variety of organisms, where they have been called "cryptic promoters" (Al-Shawi et al., 1991, *Mol. Cell. Biol.* 11, 4207–4216; Fourel et al., 1992, *Mol. Cell. Biol.* 12, 5336–5344; Irniger et al., 1992, *Nucleic Acids Res.* 20, 4733–4739; Takahashi et al., 1991, *Jpn J. Cancer Res.* 82, 1239–1244). Cryptic promoters can be found in the introns of genes, such as those encoding for yeast actin (Irniger et al., 1992, *Nucleic Acids Res.* 20, 4733–4739), and a mammalian melanoma-associated antigen (Takahashi et al., 1991, *Jpn J. Cancer Res.* 82, 1239–1244). It has been suggested that the cryptic promoter of the yeast actin gene may be a relict of a promoter that was at one time active but lost function once the coding region was assimilated into the exon-intron structure of the present-day gene (Irniger et al., 1992, *Nucleic Acids Res.* 20, 4733–4739). A cryptic promoter has also been found in an untranslated region of the second exon of the woodchuck N-myc proto-oncogene (Fourel et al., 1992, *Mol. Cell. Biol.* 12, 5336–5344). This cryptic promoter is responsible for activation of a N-myc2, a functional processed gene which arose from retropositon of N-myc transcript (Fourel et al., 1992, *Mol. Cell. Biol.* 12, 5336–5344). These types of regulatory sequences have not yet been isolated from plants.

This patent application describes, as an example, one transgenic plant, T218, generated by tagging with a promoterless GUS (β-glucuronidase) T-DNA vector. This plant is of particular interest in that GUS expression was spatially and developmentally regulated in seed coats and a promoter specific to this tissue has not been previously isolated. Cloning of the insertion site uncovered a cryptic promoter within a region of the tobacco genome not conserved among related species. This seed coat-specific promoter can be useful for controlling gene expression of selected genes to a specific stage of development.

SUMMARY OF INVENTION

The present invention is directed to a cryptic promoter identified from *Nicotiana tabacum* (tobacco). Specifically this invention relates to a seed coat-specific cryptic promoter isolated from tobacco.

The transgenic tobacco plant, T218, contained a 4.7 kb EcoRI fragment containing the 2.2 kb promoterless GUS-nos gene and 2.5 kb of 5' flanking tobacco DNA. Deletion of the region approximately between 2.5 and 1.0 kb of the 5' flanking region did not alter GUS expression, as compared to the entire 4.7 kb GUS fusion. A further deletion to 0.5 kb of the 5' flanking site resulted in complete lose of GUS activity. Thus the region between 1.0 and 0.5 of the 5' flanking region of the tobacco DNA contains the elements essential to gene activation. This region is contained within a XbaI-SnaBI restriction site fragment of the flanking tobacco DNA.

Thus according to the present invention there is provided a seed coat-specific cryptic promoter in tobacco contained within a DNA sequence, or analogue thereof, as shown in SEQ ID NO: 1.

Further according to the present invention, there is provided a DNA sequence, or analogue thereof, as shown in SEQ ID NO: 1.

This invention also relates to a cloning vector containing a seed coat-specific cryptic promoter from tobacco, which is contained within a DNA sequence, or analogue thereof, as shown in SEQ ID NO: 1 and a gene encoding a protein.

This invention also includes a plant cell which has been transformed with a cloning vector as described above.

This invention further relates to a transgenic plant containing a seed-coat specific promoter, operatively linked to a gene encoding a protein.

BRIEF DESCRIPTION OF THE DRAWINGS

FIG. 5 shows the mapping of the T218 GUS fusion termini and expression of the region surrounding the insertion site in untransformed plants.

P, untreated RNA probe; −, control assay using the probe and tRNA only; L, leaves from untransformed plants; 8, 10, 12, seeds from untransformed plants at 8, 10, and 12 dpa, respectively; T10, seeds of plant T218 at 10 dpa; +, control hybridization against unlabeled in vitro-synthesized sense RNA from subclone c (panel a) or subclone e (panel b). The two hybridizing bands near the top of the gel are end-labeled DNA fragment of 3313 and 1049 bp, included in all assays to monitor losses during processing. Molecular weight markers are in number of bases.

FIG. 6 provides the nucleotide sequence of pT218 (top line) (SEQ ID NO: 1) and pIS-1 (bottom line). Sequence identity is indicated by dashed lines. The T-DNA insertion site is indicated by a vertical line after bp 993. This site on pT218 is immediately followed by a 12 bp filler DNA, which is followed by the T-DNA. The first nine amino acids of the GUS gene and the GUS initiation codon (*) are shown. The major and minor transcriptional start site is indicated by a large and small arrow, respectively. The presumptive TATA box is identified and is in boldface. Additional putative TATA and CAAT boxes are marked with boxes. The location of direct (1–5) and indirect (6–8) repeats are indicated by arrows.

Figure 7:
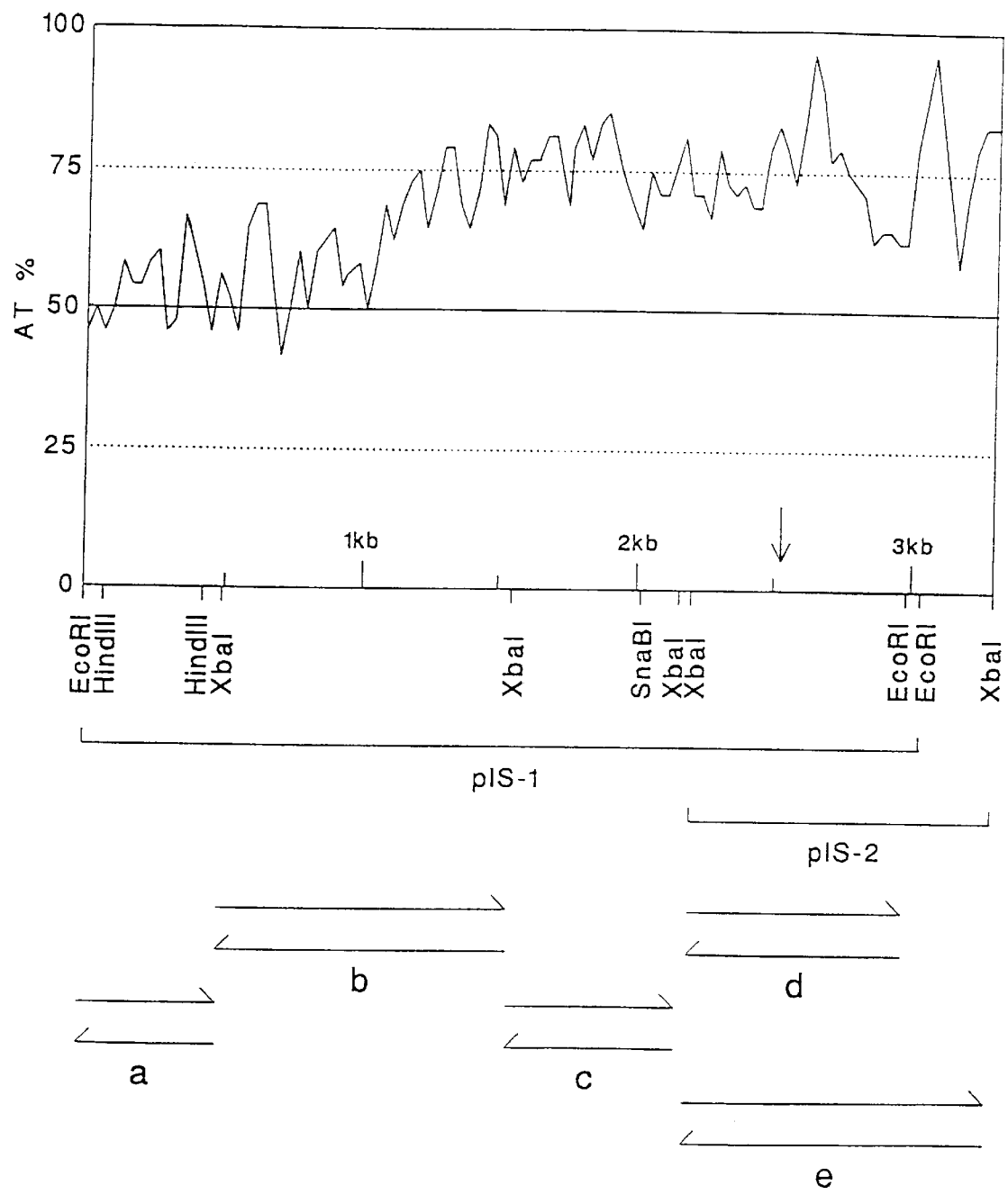

FIG. 7 shows the base composition of region surrounding the T218 insertion site cloned from untransformed plants. The site of T-DNA insertion in plant T218 is indicated by the vertical arrow. The position of the 2 genomic clones pIS-1 and pIS-2, and of the various RNA probes (a–e) used in RNase protection assays are indicated beneath the graph.

Figure 2:
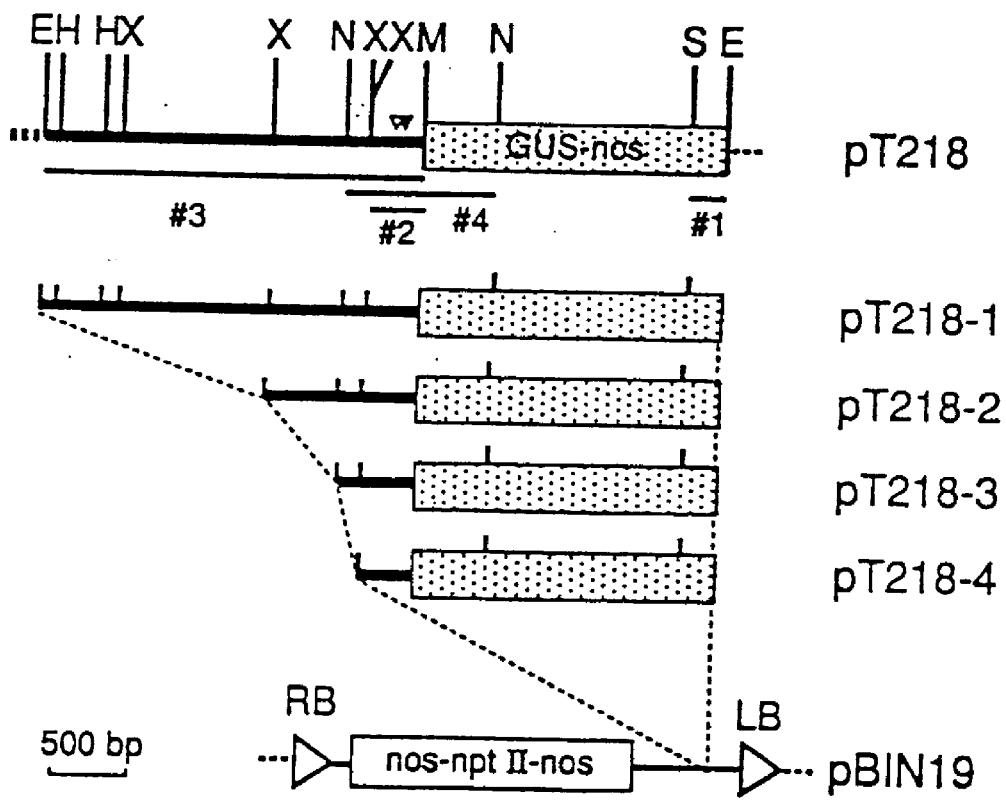
FIG. 2 shows the cloning of the GUS fusion in plant T218 (pT218) and construction of transformation vectors. Plant DNA is indicated by the solid line and the promoterless GUS-nos gene is indicated by the open box. The transcriptional start site and presumptive TATA box are located by the closed and open arrow heads respectively. DNA probes #1, 2, 3 and RNA probe #4 are shown. The EcoRI fragment in pT218 was subcloned in the pBIN19 polylinker to create pT218-1. Fragments truncated at the XbaI SnaBI and XbaI sites were also subcloned to create pT218-2, pT218-3 and pT218-4. Abbreviations for the endonuclease restriction sites are as follows: EcoRI (E), HindIII (H), XbaI (X), SnaBI (N), SmaI (M), SstI (S).
Figure 8:
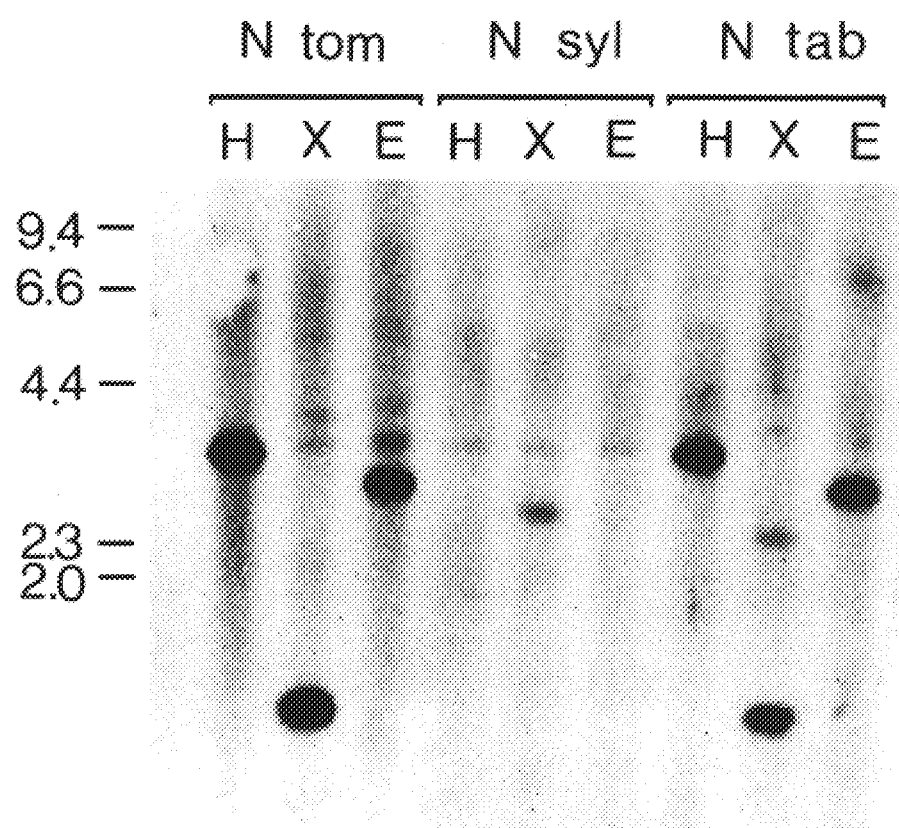

FIG. 8 shows the Southern blot analyses of the insertion site in Nicotiana species. DNA from *N. tomentosiformis* (N tom), *N. sylvestris* (N syl), and *N. tabacum* (N tab) were digested with HindIII (H), XbaI (X) and EcoRI (E) and hybridized using probe #2 (FIG. 2). Lambda HindIII markers (kb) are indicated.

Figure 9:
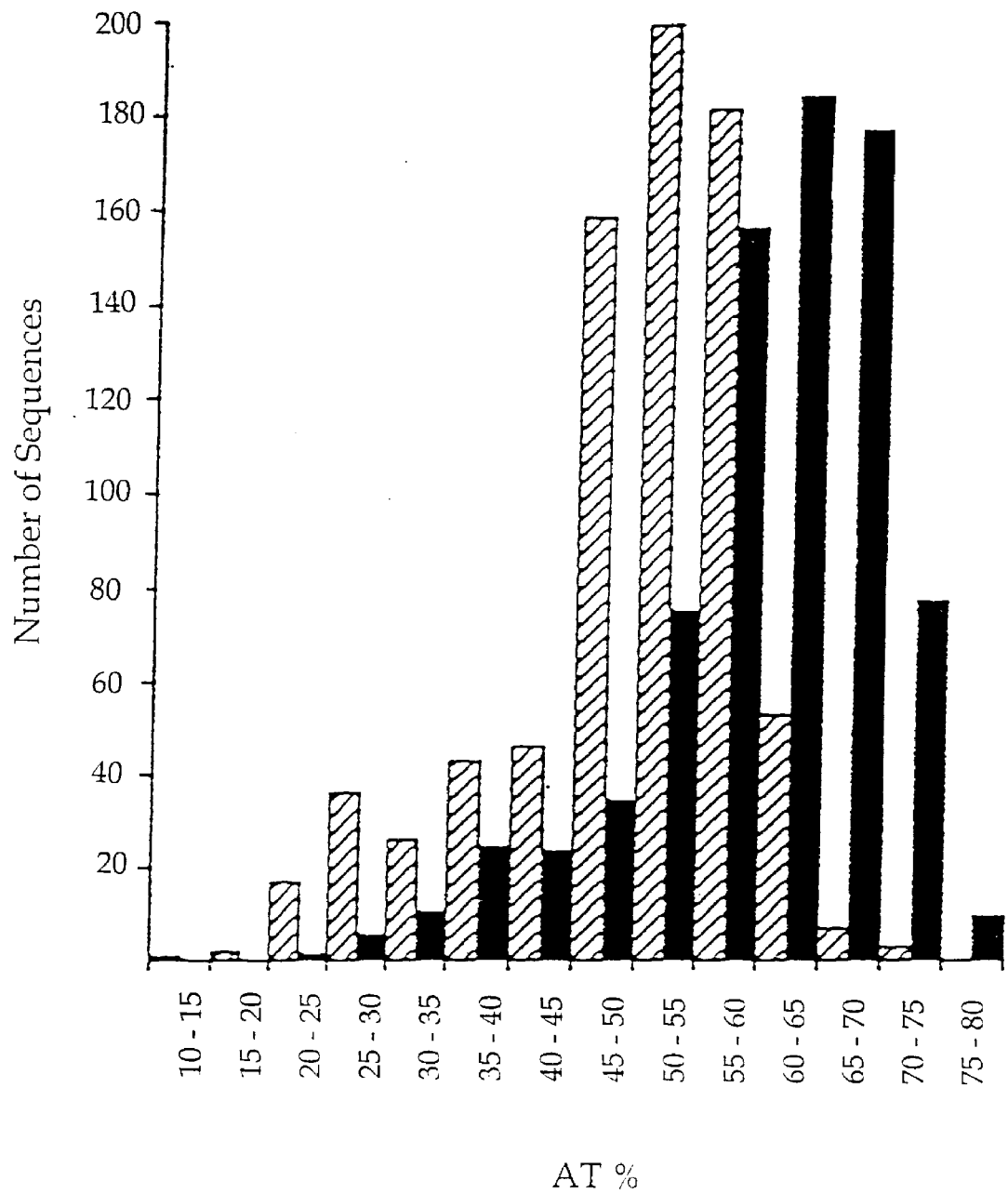

FIG. 9 shows the AT content of 5' non-coding regions of plant genes. A program was written in PASCAL to scan GenBank release 75.0 and to calculate the AT contents of the 5' non-coding (solid bars) and the coding regions (hatched bars) of all plant genes identified as "Magnoliophyta" (flowering plants). The region −200 to −1 and +1 to +200 were compared. Shorter sequences were also accepted if they were at least 190 bp long. The horizontal axis shows the ratio of the AT content (%). The vertical axis shows the number of the sequences having the specified AT content ratios.

DETAILED DESCRIPTION OF THE PREFERRED EMBODIMENTS

T-DNA tagging with a promoterless β-glucuronidase (GUS) gene generated a transgenic *Nicotiana tabacum* plant that expressed GUS activity only in developing seed coats. Cloning and deletion analysis of the GUS fusion revealed that the promoter responsible for seed coat specificity was located in the plant DNA proximal to the GUS gene. Deletion analyses localized the cryptic promoter to an approximately 0.5 kb region between a XbaI and a SnaBI restriction endonuclease site of the 5' flanking tobacco DNA. This region spans from nucleotide 1 to nucleotide 467 of SEQ ID NO: 1.

Thus, the present invention includes a DNA sequence comprising the seed coat-specific cryptic promoter from tobacco and analogues, thereof. Analogues of the cryptic promoter include any substitution, deletion, or additions of the region, provided that said analogues maintain the seed coat-specific expression activity.

The term cryptic promoter means a promoter that is not associated with a gene and thus does not control expression in its native location. These inactive regulatory sequences are buried in the genome but are capable of being functional when positioned adjacent to a gene.

The DNA sequence of the present invention thus includes the DNA sequence of SEQ ID NO: 1, the promoter region within SEQ ID NO: 1 (for example from nucleotide 1 to 476), and analogues thereof. Analogues include those DNA sequences which hybridize under stringent hybridization conditions (see Maniatis et al., in Molecular Cloning (A Laboratory Manual), Cold Spring Harbor Laboratory, 1982, p. 387–389) to the DNA sequence of SEQ ID NO: 1, provided that said sequences maintain the seed coat-specific promoter activity. An example of one such stringent hybridization conditions may be hybridization at 4XSSC at 65° C., followed by washing in 0.1XSSC at 65° C. for an hour. Alternatively an exemplary stringent hybridization condition could be in 50% formamide, 4XSSC at 42° C. Analogues also include those DNA sequences which hybridize to the sequence of SEQ ID NO: 1 under relaxed hybridization conditions, provided that said sequences maintain the seed coat-specific promoter activity. Examples of such nonhybridization conditions includes hybridization at 4XSSC at 50° C. or with 30–40% formamide at 42° C.

There are several lines of evidence that suggest that the seed coat-specific expression of GUS activity in the plant T218 is regulated by a cryptic promoter. The region surrounding the promoter and transcriptional start site for the GUS gene are not transcribed in untransformed plants. Transcription was only observed in plant T218 when T-DNA was inserted in cis. DNA sequence analysis did not uncover a long open reading frame within the 3.3 kb region cloned. Moreover, the region is very AT rich and predicted to be noncoding (data not shown) by the Fickett algorithm (Fickett, 1982, *Nucleic Acids Res.* 10, 5303–5318) as implemented in DNASIS 7.0 (Hitachi). Southern blots revealed that the insertion site is within the *N. tomentosiformis* genome and is not conserved among related species as would be expected for a region with an important gene.

As this is the first report of a cryptic promoter in plants, it is impossible to estimate the degree to which cryptic promoters may contribute to the high frequencies of promoterless marker gene activation in plants. It is interesting to note that transcriptional GUS fusions in Arabidopsis occur at much greater frequencies (54%) than translational fusions (1.6%, Kertbundit et al., 1991, *Proc. Natl. Acad. Sci. USA* 88, 5212–5216). The possibility that cryptic promoters may account for some fusions was recognized by Lindsey et al. (1993, *Transgenic Res.* 2, 33–47).

The results disclosed herewith confirms others (Gheysen et al., 1987, *Proc. Natl. Acad. Sci. USA* 84, 6169–6173 and 1991, *Genes Dev.* 5, 287–297) that T-DNA may insert into A-T rich regions as do plant transposable elements (Capel et al., 1993, *Nucleic Acids Res.* 21, 2369–2373). We illustrate that promoters of plant genes are also A-T rich raising speculation that gene insertions into these regions could facilitate the rapid acquisition of new regulatory elements during gene evolution.

The insertion of functional genes into the nuclear genome and acquisition of new regulatory sequences has already played a major role in the diversification of certain genes and the endosymbiosis of organelles. In plants, most organellar proteins are nuclear encoded due to the ongoing transfer of their genes into the nucleus (Palmer, 1991, In Bogorad L and Vasil IK (eds) The Molecular Biology of Plastids, Academic Press, San Diego, pp 5–53). Recently, it has been shown that the cox 2 gene of cowpea (Nugent and Palmer, 1991, *Cell* 66, 473–481) and soybean (Covello and Gray, 1992, *EMBO J.* 11, 3815–3820) were transferred from mitochondria to nucleus without promoters by RNA intermediates. The results disclosed herewith, with T-DNA-mediated gene fusions reveal the facility with which promoters can be acquired by incoming genes. The presence of cryptic promoters and diverse regulatory elements in the intergenic regions may insure that genes rapidly achieve the features needed to meet the demands of complex multicellular organisms.

The cryptic promoter of the present invention can also be used to control to the expression of any given gene spatially and developmentally to developing seed coats. Some examples of such uses, which are not to be considered limiting, include:

1. Modification of storage reserves in seed coats, such as starch by the expression of yeast invertase to mobilize the starch or expression of the antisense transcript of ADP-glucose pyrophosphorylase to inhibit starch biosynthesis.
2. Modification of seed color contributed by condensed tannins in the seed coats by expression of antisense transcripts of the phenylalanine ammonia lyase or chalcone synthase genes.
3. Modification of fibre content in seed-derived meal by expression of antisense transcripts of the caffeic acid-o-methyl transferase or cinnamoyl alcohol dehydrogenase genes.
4. Inhibition of seed coat maturation by expression of ribonuclease genes to allow for increased seed size, and to reduce the relative biomass of seed coats, and to aid in dehulling of seeds.
5. Expression of genes in seed coats coding for insecticidal proteins such as a-amylase inhibitor or protease inhibitor.
6. Partitioning of seed metabolites such as glucosinolates into seed coats for nematode resistant.

Thus this invention is directed to such promoter and gene combinations. Further this invention is directed to such promoter and gene combinations in a cloning vector, wherein the gene is under the control of the promoter and is capable of being expressed in a plant cell transformed with the vector. This invention further relates to transformed plant cells and transgenic plants regenerated from such plant cells. The promoter and promoter gene combination of the present invention can be used to transform any plant cell for the production of any transgenic plant. The present invention is not limited to any plant species.

While this invention is described in detail with particular reference to preferred embodiments thereof, said embodiments are offered to illustrate but not limit the invention.

EXAMPLES

Characterization of a Seed Coat-Specific GUS Fusion

Transfer of binary constructs to Agrobacterium and leaf disc transformation of *Nicotiana tabacum* SR1 were performed as described by Fobert et al. (1991, *Plant Mol. Biol.* 17, 837–851). Plant tissue was maintained on 100 µg/ml kanamycin sulfate (Sigma) throughout in vitro culture.

Nine-hundred and forty transgenic plants were produced. Several hundred independent transformants were screened for GUS activity in developing seeds using the fluorogenic assay. One of these, T218, was chosen for detailed study because of its unique pattern of GUS expression.

Fluorogenic and histological GUS assays were performed according to Jefferson (*Plant Mol. Biol. Rep.*, 1987, 5, 387–405), as modified by Fobert et al. (*Plant Mol. Biol.*, 1991, 17, 837–851). For initial screening, leaves were harvested from in vitro grown plantlets. Later flowers corresponding to developmental stages 4 and 5 of Koltunow et al. (*Plant Cell*, 1990, 2, 1201–1224) and beige seeds, approximately 12–16 dpa (Chen et al., 1988, *EMBO J.* 7, 297–302), were collected from plants grown in the greenhouse. For detailed, quantitative analysis of GUS activity, leaf, stem and root tissues were collected from kanamycin resistant F1 progeny of the different transgenic lines grown in vitro. Floral tissues were harvested at developmental stages 8–10 (Koltunow et al., 1990, *Plant Cell* 2, 1201–1224) from the original transgenic plants. Flowers of these plants were also tagged and developing seeds were collected from capsules at 10 and 20 dpa. In all cases, tissue was weighed, immediately frozen in liquid nitrogen, and stored at −80° C.

Tissues analyzed by histological assay were at the same developmental stages as those listed above. Different hand-cut sections were analyzed for each organ. For each plant, histological assays were performed on at least two different occasions to ensure reproducibility. Except for floral organs, all tissues were assayed in phosphate buffer according to Jefferson (1987, *Plant Mol. Biol. Rep.* 5, 387–405), with 1 mM X-Gluc (Sigma) as substrate. Flowers were assayed in the same buffer containing 20% (v/v) methanol (Kosugi et al., 1990, *Plant Sci.* 70, 133–140).

Figure 1:
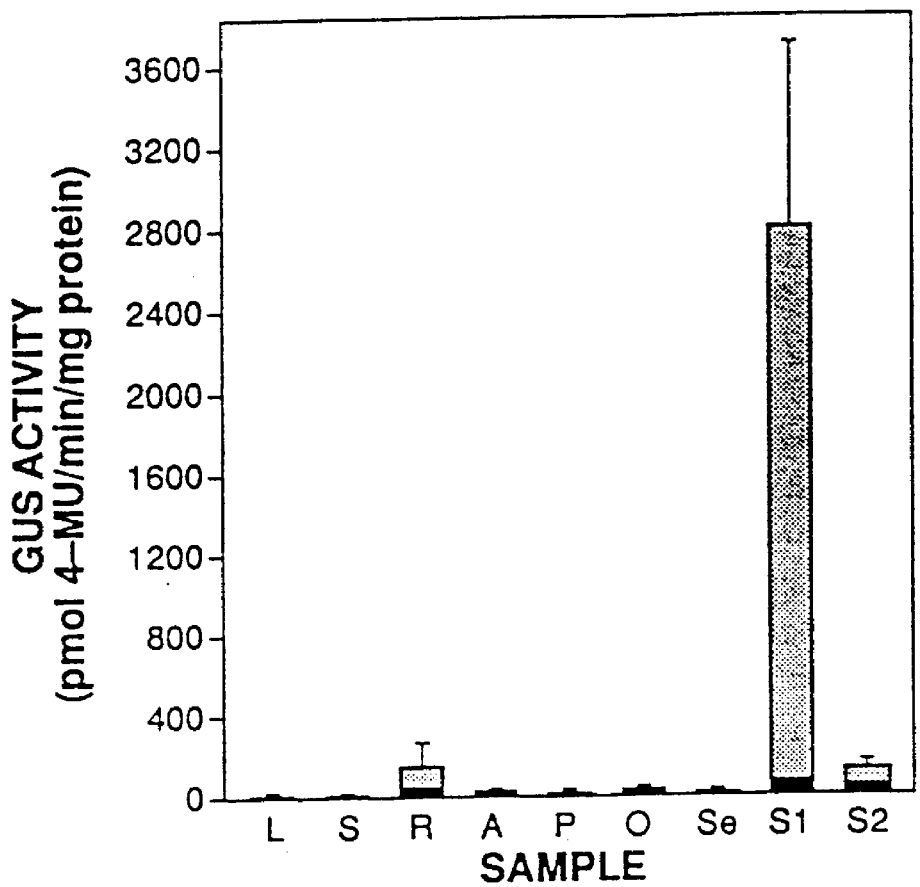
FIG. 1 depicts the fluorogenic analyses of GUS expression in the plant T218. Each bar represents the average ± one standard deviation of three samples. Nine different tissues were analyzed: leaf (L), stem (S), root (R), anther (A), petal (P), ovary (O), sepal (Se), seeds 10 days post anthesis (S1) and seeds 20 days post-anthesis (S2). For all measurements of GUS activity, the fraction attributed to intrinsic fluorescence, as determined by analysis of untransformed tissues, is shaded black on the graph. Absence of a black area at the bottom of a histogram indicates that the relative contribution of the background fluorescence is too small to be apparent.

Tissue-specific patterns of GUS expression were only found in seeds. For instance, GUS activity in plant T218 (FIG. 1) was localized in seeds from 9 to 17 days postanthesis (dpa). GUS activity was not detected in seeds at other stages of development or in any other tissue analyzed which included leaf, stem, root, anther, ovary, petal and sepal (FIG. 1). Histological staining with X-Gluc revealed that GUS expression in seeds at 14 dpa was localized in seed coats but was absent from the embryo, endosperm, vegetative organs and floral organs (results not shown).

The seed coat-specificity of GUS expression was confirmed with the more sensitive fluorogenic assay of seeds derived from reciprocal crosses with untransformed plants. The seed coat differentiates from maternal tissues called the integuments which do not participate in double fertilization (Esau, 1977, *Anatomy of Seed Plants.* New York: John Wiley and Sons). If GUS activity is strictly regulated, it must originate from GUS fusions transmitted to seeds maternally and not by pollen. As shown in Table 1, this is indeed the case. As a control, GUS fusions expressed in embryo and endosperm, which are the products of double fertilization, should be transmitted through both gametes. This is illustrated in Table 1 for GUS expression driven by the napin promoter (BngNAPI, Baszczynki and Fallis, 1990, *Plant Mol. Biol.* 14, 633–635) which is active in both embryo and endosperm (data not shown).

TABLE 1

GUS activity in seeds at 14 days post anthesis.

| Cross | | GUS Activity |
|---|---|---|
| ♀ | ♂ | nmole MU/min/mg Protein |
| T218 | T218 | 1.09 ± 0.39 |
| T218 | WP | 3.02 ± 0.19 |
| WT | T1218 | 0.04 ± 0.005 |
| WT | WT | 0.04 ± 0.005 |
| NAP-5[b] | NAP-5 | 14.6 ± 7.9 |
| NAP-5 | WT | 3.42 ± 1.60 |
| WT | NAP-5 | 2.91 ± 1.97 |

[a]WT, untransformed plants
[b]Transgenic tobacco plants with the GUS gene fused to the napin, BngNAP1, promoter (Baszczynski and Fallis, 1990, Plant Mol. Biol. 14. 633–635).

Cloning and Analysis of the Seed Coat-Specific GUS Fusion

Genomic DNA was isolated from freeze-dried leaves using the protocol of Sanders et al. (1987, *Nucleic Acid Res.* 15, 1543–1558). Ten micrograms of T218 DNA was digested for several hours with EcoRI using the appropriate manufacturer-supplied buffer supplemented with 2.5 mM spermidine. After electrophoresis through a 0.8% TAE agarose gel, the DNA size fraction around 4–6 kb was isolated, purified using the GeneClean kit (BIO 101 Inc., LaJolla, Calif.), ligated to phosphatase-treated EcoRI-digested Lambda GEM-2 arms (Promega) and packaged in vitro as suggested by the supplier. Approximately 125,000 plaques were transferred to nylon filters (Nytran, Schleicher and Schuell) and screened by plaque hybridization (Rutledge et al., 1991, *Mol. Gen. Genet.* 229, 31–40), using the 3' (termination signal) of the nos gene as probe (probe #1, FIG. 2). This sequence, contained in a 260 bp SstI/EcoRI restriction fragment from pPRF-101 (Fobert et al., 1991, *Plant Mol. Biol.* 17, 837–851), was labeled with [$\alpha$-$^{32}$P]-dCTP (NEN) using random priming (Stratagene). After plaque purification, phage DNA was isolated (Sambrook et al., 1989, *A Laboratory Manual.* New York: Cold Spring Harbor Laboratory Press), mapped and subcloned into pGEM-4Z (Promega). The EcoRI fragment and deletions shown in FIG. 2 were inserted into pBIN19 (Bevan, 1984, *Nucl. Acid Res.* 12, 8711–8721). Restriction mapping was used to determine the orientation of the fusion in pBIN19 and to confirm plasmid integrity. Plants were transformed with a derivative which contained the 5' end of the GUS gene distal to the left border repeat. This orientation is the same as that of the GUS gene in the binary vector pBl101 (Jefferson, 1987, *Plant Mol. Biol. Rep.* 5, 387–405).

The GUS fusion in plant T218 was isolated as a 4.7 kb EcoRI fragment containing the 2.2 kb promoterless GUS-nos gene at the T-DNA border of pPRF120 and 2.5 kb of 5' flanking tobacco DNA (pT218, FIG. 2), using the nos 3' fragment as probe (probe #1, FIG. 2). To confirm the ability of the flanking DNA to activate the GUS coding region, the entire 4.7 kb fragment was inserted into the binary transformation vector pBIN19 (Bevan, 1984, *Nucl. Acid Res.* 12, 8711–8721), as shown in FIG. 2. Several transgenic plants were produced by Agrobacterium-mediated transformation of leaf discs. Southern blots indicated that each plant contained 1–4 T-DNA insertions at unique sites. The spatial patterns of GUS activity were identical to that of plant T218. Histologically, GUS staining was restricted to the seed coats of 14 dpa seeds and was absent in embryos and 20 dpa seeds (results not shown). Fluorogenic assays of GUS activity in developing seeds showed that expression was restricted to seeds between 10 and 17 dpa, reaching a maximum at 12 dpa (FIG. 3($a$) and 3($b$)). The 4.7 kb fragment therefore contained all of the elements required for the tissue-specific and developmental regulation of GUS expression.

Figures 3A, 3B:
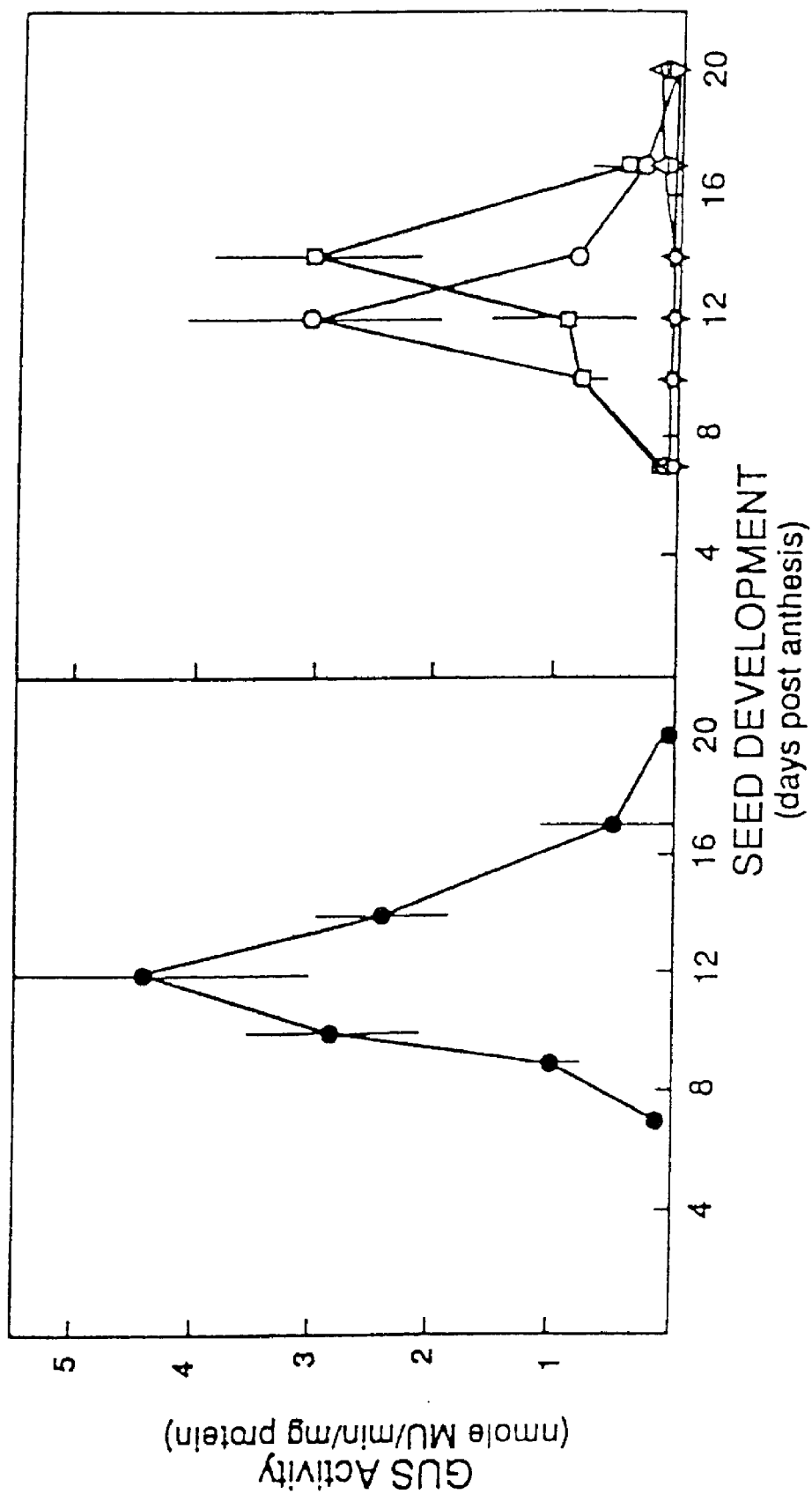
FIG. 3 shows the expression pattern of promoter fusions during seed development. GUS activity in developing seeds (4–20 days postanthesis (dpa)) of (FIG. 3a) plant T218 (●-●) and (FIG. 3b) plants transformed with vectors pT218-1 (○-○), pT218-2 (□-□), pT218-3 (▽-▽) and pT218-4 (A-A) which are illustrated in FIG. 2. The 2 day delay in the peak of GUS activity during seed development, seen with the pT218-2 transformant, likely reflects greenhouse variation conditions.
Figure 4:
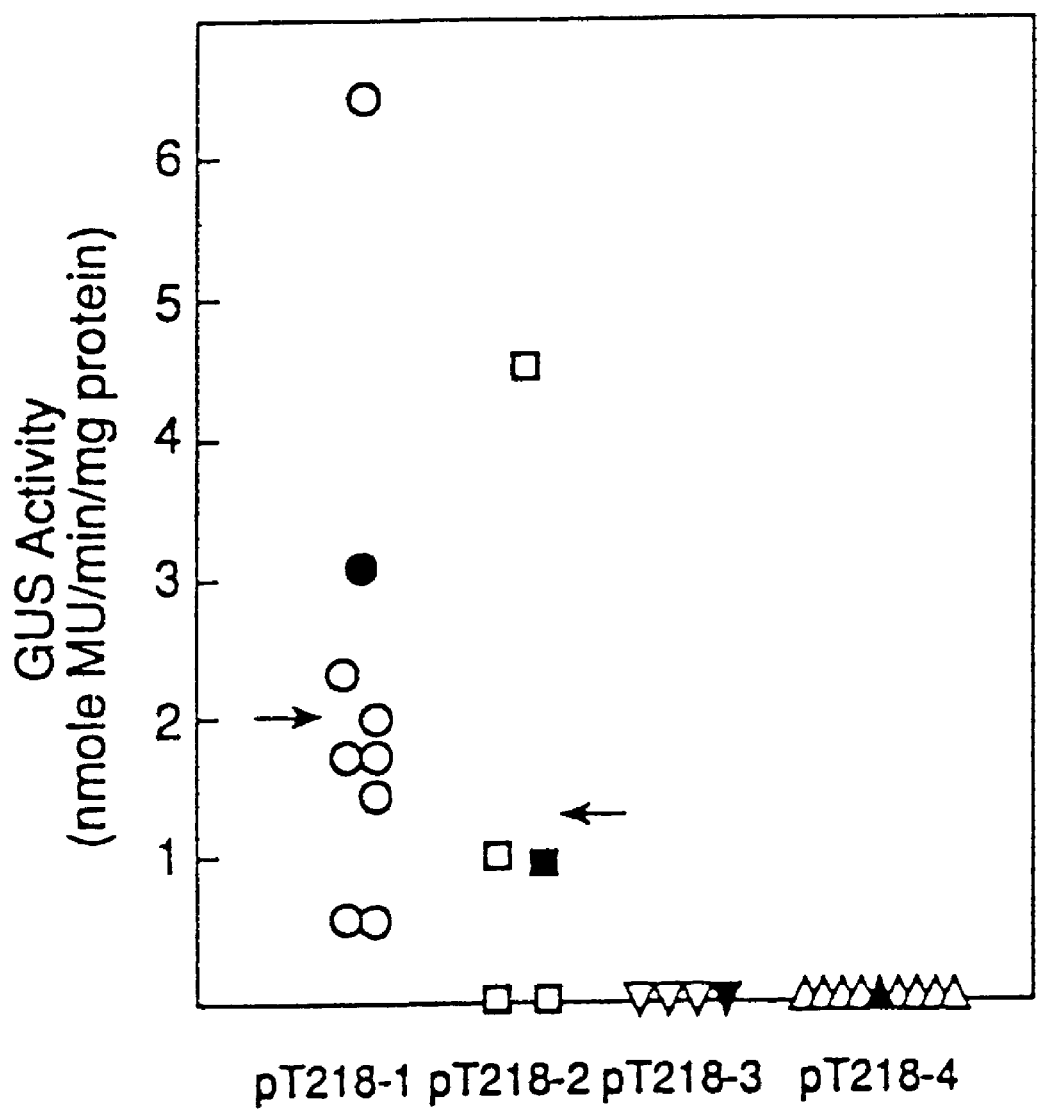
FIG. 4 shows GUS activity in 12 dpa seeds of independent transformants produced with vectors pT218-1 (○), pT218-2 (□), pT218-3 (▽) and pT218-4 (Δ). The solid markers indicate the plants shown in FIG. 3(b) and the arrows indicate the average values for plants transformed with pT218-1 or pT218-2.

To locate regions within the flanking plant DNA responsible for seed coat-specificity, truncated derivatives of the GUS fusion were generated (FIG. 2) and introduced into tobacco plants. Deletion of the region approximately between 2.5 and 1.0 kb, 5' of the insertion site (pT218-2, FIG. 2) did not alter expression compared with the entire 4.7 kb GUS fusion (FIGS. 3$b$ and 4). Further deletion of the DNA, to the SnaBI restriction site approximately 0.5 kb, 5' of the insertion site (pT218-3, FIG. 2), resulted in the complete loss of GUS activity in developing seeds (FIGS. 3$b$ and 4). This suggests that the region approximately between 1.0 and 0.5 kb, 5' of the insertion site contains elements essential to gene activation. GUS activity in seeds remained absent with more extensive deletion of plant DNA (pT218-4, FIGS. 2, 3$b$ and 4) and was not found in other organs including leaf, stem, root, anther, petal, ovary or sepal from plants transformed with any of the vectors (data not shown).

Figures 5A, 5B:
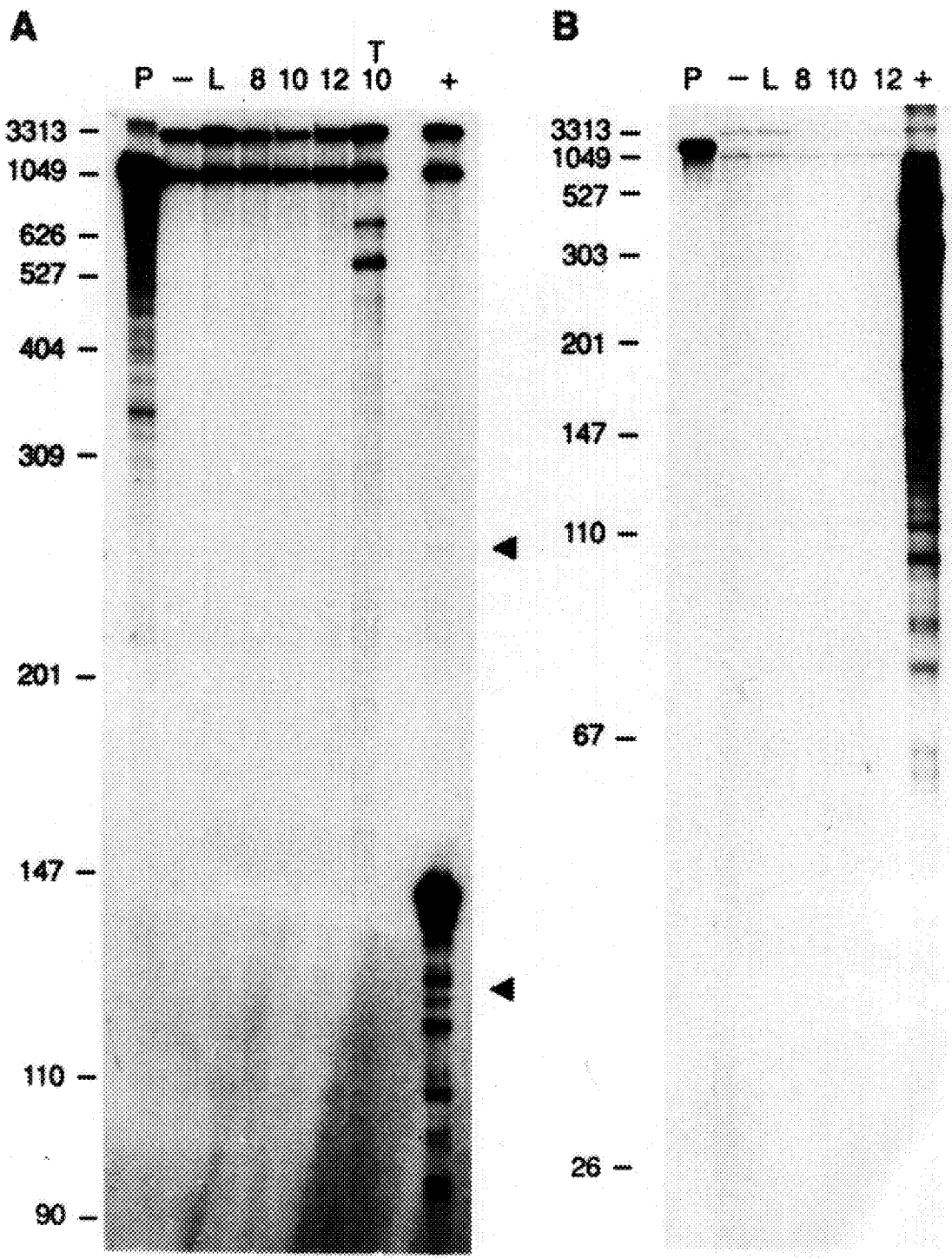
(FIG. 5a)
Mapping of the GUS mRNA termini in plant T218. The antisense RNA probe from subclone #4 (FIG. 2) was used for hybridization with total RNA of tissues from untransformed plants (10 μg) and from plant T218 (30 μg). Arrowheads indicate the anticipated position of protected fragments if transcripts were initiated at the same sites as the T218 GUS fusion.
(FIG. 5b)
RNase protection assay using the antisense (relative to the orientation of the GUS coding region) RNA probe from subclone e (FIG. 7) against 30 μg total RNA of tissues from untransformed plants.

The transcriptional start site for the GUS gene in plant T218 was determined by RNase protection assays with RNA probe #4 (FIG. 2) which spans the T-DNA/plant DNA junction. For RNase protection assays, various restriction fragments from pIS-1, pIS-2 and pT218 were subcloned into the transcription vector pGEM-4Z as shown in FIGS. 7 and 2, respectively. A 440 bp HindIII fragment of the tobacco acetohydroxyacid synthase SURA gene was used to detect SURA and SURB mRNA. DNA templates were linearized and transcribed in vitro with either T7 or SP6 polymerases to generate strand-specific RNA probes using the Promega transcription kit and [$\alpha$-$^{32}$P]CTP as labeled nucleotide. RNA probes were further processed as described in Ouellet et al. (1992, *Plant J.* 2, 321–330). RNase protection assays were performed as described in Ouellet et al., (1992, *Plant J.* 2, 321–330), using 10–30 µg of total RNA per assay. Probe digestion was done at 30° C. for 15 min using 30 µg ml$^{-1}$ RNase A (Boehringer Mannheim) and 100 units ml$^{-1}$ RNase T1 (Boehringer Mannheim). FIG. 5 shows that two termini were mapped in the plant DNA. The major 5' terminus is situated at an adenine residue, 122 bp upstream of the T-DNA insertion site (FIG. 6). The sequence at this transcriptional start site is similar to the consensus sequence for plant genes (C/TTC↓ATCA; Joshi, 1987 *Nucleic Acids Res.* 15, 6643–6653). A TATA box consensus sequence is present 37 bp upstream of this start site (FIG. 6). The second, minor terminus mapped 254 bp from the insertion site in an area where no obvious consensus motifs could be identified (FIG. 6).

The tobacco DNA upstream of the insertion site is very AT-rich (>75%, see FIG. 7). A search for promoter-like motifs and scaffold attachment regions (SAR), which are often associated with promoters (Breyne et al., 1992, *Plant Cell* 4, 463–471; Gasser and Laemmli, 1986, *Cell* 46, 521–530), identified several putative regulatory elements in the first 1.0 kb of tobacco DNA flanking the promoterless GUS gene (data not shown). However, the functional significance of these sequences remains to be determined.

Cloning and Analysis of the Insertion Site from Untransformed Plants

A lambda DASH genomic library was prepared from DNA of untransformed *N. tabacum* SR1 plants by Stratagene for cloning of the insertion site corresponding to the gene fusion in plant T218. The screening of 500,000 plaques with probe #2 (FIG. 2) yielded a single lambda clone. The EcoRI and XbaI fragments were subcloned in pGEM-4Z to generate pIS-1 and pIS-2. FIG. 7 shows these two overlapping subclones, pIS-1 (3.0 kb) and pIS-2 (1.1 kb), which contain tobacco DNA spanning the insertion site (marked with a vertical arrow). DNA sequence analysis (using dideoxy nucleotides in both directions) revealed that the clones, pT218 and pIS-1, were identical over a length of more than 2.5 kb, from the insertion site to their 5' ends, except for a 12 bp filler DNA insert of unknown origin at the T-DNA border (FIG. 6 and data not shown). The presence of filler DNA is a common feature of T-DNA/plant DNA junctions (Gheysen et al., 1991, *Gene* 94, 155–163). Gross rearrangements that sometimes accompany T-DNA insertions (Gheysen et al., 1990, *Gene* 94, 155–163; and 1991, *Genes Dev.* 5, 287–297) were not found (FIG. 6) and therefore could not account for the promoter activity associated with this region. The region of pIS-1 and pIS-2, 3' of the insertion site is also very AT-rich (FIG. 7).

To determine whether there was a gene associated with the pT218 promoter, more than 3.3 kb of sequence contained with pIS-1 and pIS-2 was analyzed for the presence of long open reading frames (ORFs). However, none were detected in this region (data not shown). To determine whether the region surrounding the insertion site was transcribed in untransformed plants, Northern blots were performed with RNA from leaf, stem, root, flower and seeds at 4, 8, 12, 14, 16, 20 and 24 dpa. Total RNA from leaves was isolated as described in Ouellet et al., (1992, *Plant J.* 2, 321–330). To isolate total RNA from developing seeds, 0.5 g of frozen tissue was pulverized by grinding with dry ice using a mortar and pestle. The powder was homogenized in a 50 ml conical tube containing 5 ml of buffer (1M Tris HCl, pH 9.0, 1% SDS) using a Polytron homogenizer. After two extractions with equal volumes of phenol:chloroform:isoamyl alcohol (25:24:1), nucleic acids were collected by ethanol precipitation and resuspended in water. The RNA was precipitated overnight in 2M LiCl at 0° C., collected by centrifugation, washed in 70% ethanol and resuspended in water. Northern blot hybridization was performed as described in Gottlob-McHugh et al. (1992, *Plant Physiol.* 100, 820–825). Probe #3 (FIG. 2) which spans the entire region of pT218 5' of the insertion did not detect hybridizing RNA bands (data not shown). To extend the sensitivity of RNA detection and to include the region 3' of the insertion site within the analysis, RNase protection assays were performed with 10 different RNA probes that spanned both strands of pIS-1 and pIS-2 (FIG. 7). Even after lengthy exposures, protected fragments could not be detected with RNA from 8, 10, 12 dpa seeds or leaves of untransformed plants (see FIG. 5 for examples with two of the probes tested). The specific conditions used allowed the resolution of protected RNA fragments as small as 10 bases (data not shown). Failure to detect protected fragments was not due to problems of RNA quality, as control experiments using the same samples detected acetohydroxyacid synthase (AHAS) SURA and SURB mRNA which are expressed at relatively low abundance (data not shown). Conditions used in the present work were estimated to be sensitive enough to detect low-abundance messages representing 0.001–0.01% of total mRNA levels (Ouellet et al., 1992, *Plant J.* 2, 321–330). Therefore, the region flanking the site of T-DNA insertion does not appear to be transcribed in untransformed plants.

Genomic Origins of the Insertion Site

Southern blots were performed to determine if the insertion site is conserved among Nicotiana species. Genomic DNA (5 μg) was isolated, digested and separated by agarose gel electrophoresis as described above. After capillary transfer on to nylon filters, DNA was hybridized, and probes were labeled, essentially as described in Rutledge et al. (1991, *Mol. Gen. Genet.* 229, 31–40). High-stringency washes were in 0.2×SSC at 65° C. while low-stringency washes were in 2×SSC at room temperature. In FIG. 8, DNA of the allotetraploid species *N. tabacum* and the presumptive progenitor diploid species *N. tomentosiformis* and *N. sylvestris* (Okamuro and Goldberg, 1985, *Mol. Gen. Genet.,* 198, 290–298) were hybridized with probe #2 (FIG. 2). Single hybridizing fragments of identical size were detected in *N. tabacum* and *N. tomentosiformis* DNA digested with HindIII, XbaI and EcoRI, but not in *N. sylvestris.* Hybridizations with pIS-2 (FIG. 8) which spans the same region but includes DNA 3' of the insertion site yielded the same results. They did not reveal hybridizing bands, even under conditions of reduced stringency, in additional Nicotiana species including *N. rustica, N. glutinosa, N. megalosiphon* and *N. debneyi* (data not shown). Probe #3 (FIG. 2) revealed the presence of moderately repetitive DNA specific to the *N. tomentosiformis* genome (data not shown). These results suggest that the region flanking the insertion site is unique to the *N. tomentosiformis* genome and is not conserved among related species as might be expected for regions that encode essential genes.

All scientific publications and patent documents are incorporated herein by reference.

The present invention has been described with regard to preferred embodiments. However, it will be obvious to persons skilled in the art that a number of variations and modifications can be made without departing form the scope of the invention as described in the following claims.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 1070
        ( B ) TYPE: Nucleic Acid
        ( C ) STRANDEDNESS: Double- Stranded
        ( D ) TOPOLOGY: Linear ( i i ) MOLECULE TYPE: Genomic DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Nicotiana tabacum ( v i i ) IMMEDIATE SOURCE:
        ( A ) LIBRARY:
        ( B ) CLONE: plasmid pT218

( v i i i ) POSITION IN GENOME:

( i x ) FEATURE:

( x ) PUBLICATION INFORMATION:
        ( A ) AUTHORS: Pierre R. Fobert, H l ne Labb , John
            Cosmopoulos, Sylvia Gottlob-McHugh, Th r se
            Ouellet, Jiro Hattori, Glen Sunohara, V.N.
            Iyer, Brian L. Miki
        ( B ) TITLE: T-DNA Tagging of a Seed Coat-Specific
            Cryptic Promotor in Tobacco
        ( C ) JOURNAL: The Plant Journal
        ( D ) VOLUME: 6
        ( E ) ISSUE: 4
        ( F ) PAGES: 567-577
        ( G ) DATE: 1994
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 1:

```
TCTAGACTTG  TCTTTTCTTT  ACATAATCCT  CTTCTTCTTT  TTTTTGTTAG  TTTCTTCTGT      60

TTTATCCAAA  AAACGAATTA  TTGATTAAGA  AATACACCAG  ACAAGTTTTT  TACTTCTTTT     120

TCTTTTTTTT  TTTGTGGTAA  AAAATTACAC  CTGGACAAGT  TTATCACGAA  AATGAAAATT     180

GCTATTTAAG  GGATGTAGTT  CCGGACTATT  TGGAAGATAA  GTGTTAACAA  AATAAATAAA     240

TAAAAGTTT   ATACAGTTAG  ATCTCTCTAT  AACAGTCATC  CTTATTTATA  ACAATACTTT     300

ACTATAACCG  TCAAATTTAT  TTGAAACAA   AATTTTCATG  TTATGTTACT  ATAACAGTAT     360

TTTATTATAG  CAACCAAAAA  ATATCGAAAC  AGATACGATT  GTTATAGAGC  GATTTGATTG     420

TATCATTATC  CACATATTTT  CGTAAGCCCA  ATTACTCCTC  CTACGTACGA  TGAAAGTAAA     480

CCAATTTAAA  GTTGCAAAAA  TCCAATAGAT  TTCAATACTT  CTTCAACTGG  CGTTATGTTA     540

GGTAATGACT  CCTTTTTAAC  TTTTCATCTT  TAATTTGAAG  TTTCTTTCAT  TAAAAGAAAG     600

TTTCTAGAAG  AGAAGTGTTT  TAACACTTCT  AGCTCTACTA  TTATCTGTGT  TTCTAGAAGA     660

AAAATAGAAA  ATGTGTCCAC  CTCAAAAACA  ACTAAAGGTG  GGCAAATCTC  CACCTATTTA     720

TTTTATTTTG  GATTAATTAA  GATATAGTAA  AGATCAGTTA  TAAACGGAGT  TTTGAGTTGA     780
```

-continued

| | | | | | | |
|---|---|---|---|---|---|---|
| TACAGTGAAT | TTTAAGATGT | GTACCGATTT | AACTTTATTT | ACATTTATGT | TTCGCACATA | 840 |
| TAAGAAGTCC | GATTTGGAAA | TACTAGATTT | TGTCAATCAG | GCAATTCATG | TGGTTGAAGA | 900 |
| ATTTAAGTTA | TATACAATGA | TGATATAAAG | AATTTTATA | CTATTAGTGC | AAATTAATCG | 960 |
| ATTACTAAAA | ATTATTATTC | TATTAATTTA | TGCTATCGTG | CCTCCCAAC | CCGTCGACCG | 1020 |
| CGGTACCCGG | TGGTCAGTCC | CTT ATG TTA | CGT CCT GTA | GAA ACC CCA ACC | | 1070 |

We claim:

1. An isolated DNA sequence having a seed coat-specific cryptic promoter region comprised of either nucleotides 1–467 of SEQ ID NO: 1 or an analogue of said nucleotides 1–467 of SEQ ID NO: 1, wherein said analogue hybridizes under stringent conditions to nucleotides 1-467 of SEQ ID NO: 1.

2. A cloning vector which comprises a DNA region that is transcribed into RNA, and a seed coat-specific cryptic promoter of claim 1, wherein the DNA region is under the control of the promoter and is capable of being expressed in a plant cell transformed with the vector.

3. A plant cell which has been transformed with the vector as claimed in claim 2.

4. A transgenic plant containing a promoter as claimed in claim 1, operatively linked to a gene encoding a protein.

5. A transgenic plant containing a vector as claimed in claim 2.

6. An isolated DNA sequence having a seed coat-specific cryptic promoter region comprised of nucleotides 1–467 of SEQ ID NO: 1.

7. A cloning vector which comprises a DNA region that is transcribed into RNA, and a seed coat-specific cryptic promoter according to claim 6, wherein the DNA region is under the control of the promoter and is capable of being expressed in a plant cell transformed with the vector.

8. A plant cell which has been transformed with a cloning vector of claim 7.

9. A transgenic plant containing a seed coat-specific promoter according to claim 6, operatively linked to a gene encoding a protein.

* * * * *

UNITED STATES PATENT AND TRADEMARK OFFICE
CERTIFICATE OF CORRECTION

PATENT NO. : 5,824,863
DATED : October 20, 1998
INVENTOR(S) : Miki et al.

It is certified that error appears in the above-identified patent and that said Letters Patent is hereby corrected as shown below:

ON THE TITLE PAGE:

ITEM [75] Inventors: Delete "V.N. Iyer, Saskatoon" and replace with --Venkatram N. Iyer, Ottawa--, and after "Pierre Fobert," delete "Ottawa" and replace with --Saskatoon--.

After ITEM "[22] Filed: May 15, 1995", insert the following ITEM: --[30] Foreign Application Priority Data: May 09, 1995 [CA] Canada .......... 2,149,000--.

Signed and Sealed this

Twentieth Day of June, 2000

Attest:

Q. TODD DICKINSON

*Attesting Officer*    *Director of Patents and Trademarks*